United States Patent [19]

Callne

[11] Patent Number: 5,181,849
[45] Date of Patent: Jan. 26, 1993

[54] ARTICULATING PAPER HOLDER

[76] Inventor: Lars E. Callne, 110 Los Patios, Los Gatos, Calif. 95030

[21] Appl. No.: 819,489

[22] Filed: Jan. 10, 1992

[51] Int. Cl.[5] .............................................. A61C 3/00
[52] U.S. Cl. .................................... 433/153; 433/157
[58] Field of Search ................. 433/70, 152, 153, 157, 433/163, 162

[56] References Cited

U.S. PATENT DOCUMENTS

| | | | |
|---|---|---|---|
| 1,464,807 | 8/1923 | Clark | 433/157 X |
| 1,910,740 | 5/1933 | Barsha | 433/70 X |
| 2,602,227 | 7/1952 | Kemppe | 433/157 |
| 3,046,658 | 7/1962 | Joffe | 433/70 |
| 4,225,667 | 9/1980 | Ruben | 433/162 |
| 4,340,369 | 7/1982 | Steiner et al. | 433/162 |
| 4,995,361 | 2/1991 | Lorenzana et al. | 132/323 X |

FOREIGN PATENT DOCUMENTS 273811  5/1951  Switzerland ........................ 433/162

*Primary Examiner*—Gene Mancene
*Assistant Examiner*—Nicholas D. Lucchesi
*Attorney, Agent, or Firm*—Thomas E. Schatzel

[57] ABSTRACT

The present invention comprises an articulating paper holder which has an elongated handle and an elongated holding arm. The holding arm is securely attached to and extends from the handle. The holding arm includes a holding means for securely holding a piece of articulating paper for imprinting occlusion contact patterns. Specifically, in a preferred embodiment, the elongated handle and arm are composed of plastic material whereby the articulating paper holder can be inexpensively mass produced and is therefore disposable.

15 Claims, 1 Drawing Sheet

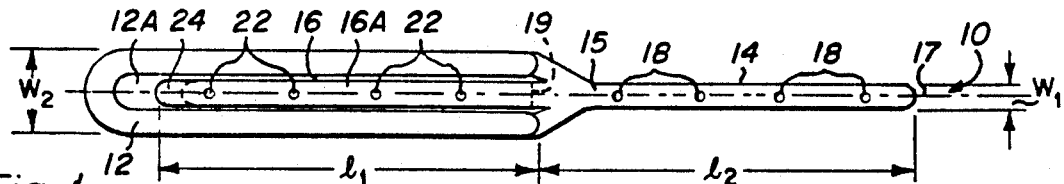
Fig_1
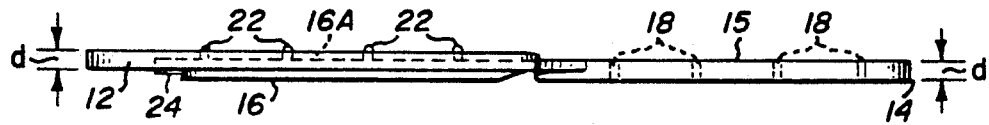
Fig_2
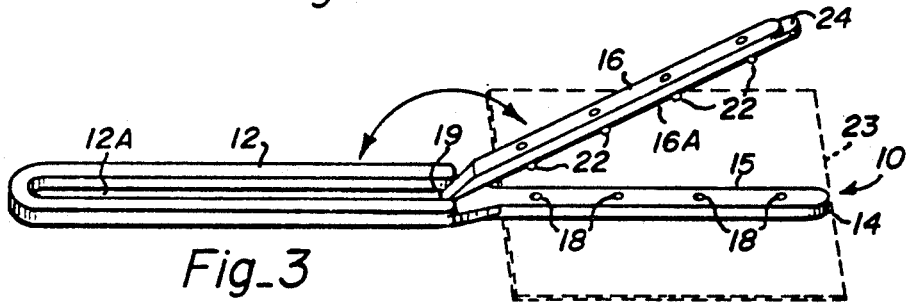
Fig_3
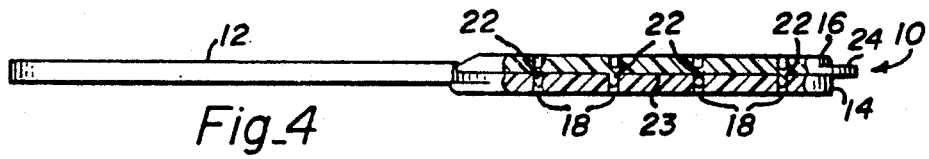
Fig_4
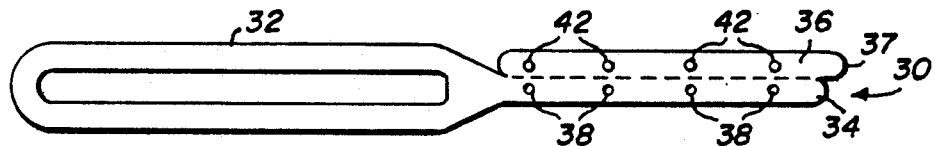
Fig_5
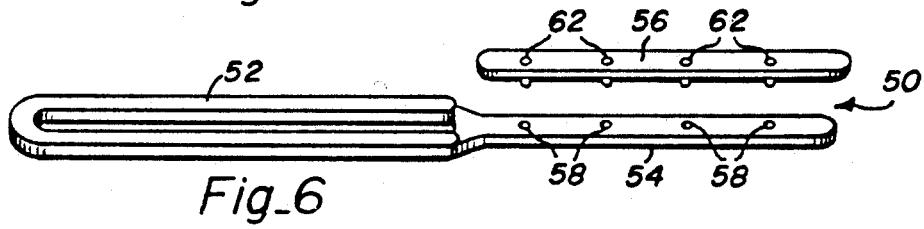
Fig_6
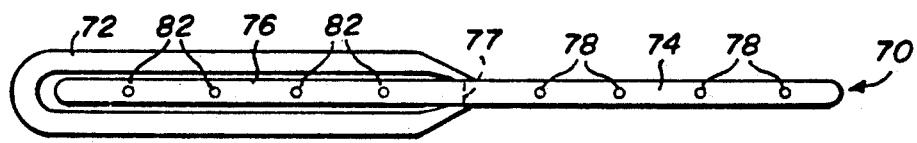
Fig_7A
Fig_7B

ARTICULATING PAPER HOLDER

BACKGROUND OF THE INVENTION

1. Field of the Invention

This inventions relates generally to a dental apparatus for imprinting the occlusal contact to determine if adjustment need to be made to correct occlusal interference or deflection. More particularly, this invention relates to an articulating paper holder which is light, disposable, inexpensive, and can be conveniently mass produced.

2. Description of the Prior Art

The performance of a dental articulation imprint for marking the tooth contact points on occlusion requires a dentist to place into a patient's mouth an articulation paper by use of a pair of articulating forceps. After the tooth contact points are marked, the articulating paper is removed from the forceps for further measurements and processing by the dentist. The articulating paper forceps are sterilized for repeated application with another patient. The repeated use of articulating forceps inside the mouth of many patients raises the concerns that it may increase the probability of disease transmissions. Such concerns have been heightened by the recent fear of widespread Human Immunodeficiency virus (HIV). Such fears may not be totally baseless since many dental problems often involve dental bleeding.

U.S. Pat. No. 4,340,369 by Steiner et al., entitled "Dental Articulating Paper Forceps" (Jul. 20, 1982) discloses a dental articulating forceps which has a pair of opposed long thin jaws extending from interconnected spring arms. The face of one jaw is directed toward the other jaw. The inner face of one jaw has grooves while the other jaw has ridges matching the grooves whereby when the spring arms force these two opposite jaws to engage each other the articulating paper is securely held. A commercial product is produced according to one of the preferred embodiments disclosed in this patent. A special stainless steel approved by the U.S. Federal Food and Drug Administration (FDA) is used for the manufacture of the articulating forceps. It serves the function of assisting the dentist in introducing the articulating papers into the mouth of a patient. However, due to its manufacture cost, it is repeatedly used. Therefore, an administrative procedure has to be established to assure that the forceps are properly sterilized after each use. The operation cost is thus increased. Additionally, the probability of negligence in the administration of the sterilization procedures may cause inadvertent transmission of diseases leading to potentially severe consequences.

As more and more stringent sterilization requirements and protective measures are being imposed on dental practice, and considering the risk of malpractice suits if severe consequences are caused by a negligence in sterilizing the forceps, the use of stainless steel forceps is limited by its high manufacture cost and the potential risks involved due to its repeated use.

SUMMARY OF THE PRESENT INVENTION

It is therefore an object of the present invention to provide an articulating paper holder which is disposable whereby the possibility of disease transmission caused by re-use of an articulating holder may be minimized.

It is another object of this invention to provide a disposable articulating paper holder which is simple in its design and can be inexpensively mass produced.

A further object of the present invention is to provide an articulating paper holder which is lightweight and can be conveniently applied for imprinting the occlusal patterns.

It is a further object of the present invention to provide an articulating paper holder which can firmly hold the articulating paper to produce accurate occlusal contact imprints.

Briefly, in a preferred embodiment, the present invention comprises an articulating paper holder which has an elongated handle and an elongated holding arm. The holding arm is securely attached to and extends from the handle. The holding arm includes a holding means for securely holding a piece of articulating paper for imprinting the occlusion contact patterns. Specifically, in a preferred embodiment, the elongated handle and arm are composed of plastic materials whereby the articulating paper can be inexpensively mass produced and is therefore disposable.

An advantage of the present invention is that it provides a disposable articulating paper holder whereby the probability of transmission of diseases caused by re-use of articulating holders is minimized.

Another advantage of the present invention is that it provides a disposable articulating paper holder which has a simple design and can be inexpensively mass produced.

Another advantage of the present invention is that it provides an articulating paper holder which is light in weight and can be conveniently applied for imprinting the occlusal patterns.

Another advantage of the present invention is that it provides an articulating paper holder which can firmly hold the articulating paper to produce accurate occlusal contact imprints.

These and other objects and advantages of the present invention will no doubt become obvious to those of ordinary skill in the art after having read the following detailed description of the preferred embodiment which is illustrated in the various drawing figures.

BRIEF DESCRIPTION OF THE DRAWINGS

FIG. 1 is a top view of an articulating paper holder according to a preferred embodiment of the present invention;

FIG. 2 is a side view of the articulating paper holder of FIG. 1;

FIG. 3 is a perspective view of the articulating paper holder of FIG. 1 showing the motion of a locking arm for locking to the holding arm;

FIG. 4 is a side view, partially sectional, of the articulating paper holder of FIG. 1 with the locking arm locked to the holding arm and with articulation paper in place;

FIG. 5 is a top view of an articulating paper holder according to an alternative preferred embodiment of the present invention;

FIG. 6 is a top view of an articulating paper holder according to another alternative preferred embodiment of the present invention;

FIG. 7A is a top view of a foldable articulating paper holder according to a preferred embodiment of the present invention where the holding arm and the locking arm are deplored in their extending position; and FIG. 7B is a top view of a foldable articulating paper holder of FIG. 7A where the holding arm and the locking arm are folded.

DETAILED DESCRIPTION OF THE PREFERRED EMBODIMENT

FIGS. 1 and 2 are the top and side view, respectively, of an articulating paper holder 10 in accordance with a preferred embodiment of the present invention. The paper holder 10 comprises an elongated, oblong handle 12 with a hollow internal area 12A attached to an elongated holding arm 14 having a smooth facial surface 15 and extending forward from handle 12. Within the interior of handle 12 is a locking arm 16, having a smooth facial surface 16A and aligned with holding arm 14 such that centerline 17 of the arm 14 and locking arm 16 coincide.

Holding arm 14 and locking arm 16 further include a locking means to firmly hold an articulating paper between holding arm 14 having a smooth facial surface 15 and locking arm 16 such that the articulating paper may be introduced into a patient's mouth for marking the tooth contact points on occlusion. As shown in FIGS 1. and 2, the locking means includes a plurality of dents 18 disposed on holding arm 14 along the centerline 17 and a plurality of corresponding buttons 22 disposed on locking arm 16 along the centerline 17. FIG. 3 shows a perspective view of holder 10 where locking arm 16 is being deplored as it is urged toward the holding arm 14 in a direction as that shown by the arrow. The arm 16 pivots about a fold line 19 included at the common structure of the handle 12 and arm 16. As the locking arm 16 is urged towards the holding arm 14, each button 22 approaches to interlock with a corresponding dent 18 for securely locking articulating paper 23 in place. FIG. 4 shows a cross-sectional view of the paper holder 10 as the locking arm 16 is locked to the holding arm 14. Each button 22 is securely interlocked with a corresponding dent 18. The cross-sectional diameter of button 22 is slightly larger than that at the entry of dent 18 such that buttons 22 can be easily inserted into and securely locked inside the dents 18 under the finger pressure of an individual. Also, the material of the arms 14 and 16 are such that the dents 18 are slightly expandable under hand pressure such that locking arm 16 can be unlocked by hand in applying a pulling force to the locking arm 16 about a tab 24 integral to the arm 16 to remove the buttons 22 from the dents 18. Therefore, the articulating paper 23, after being locked in place, may be removed under pressure by unlocking the locking arm 16 from the holding arm 14. Thus, this allows the dentist to readjust the holding position of the articulating paper 23 and then relock it again to the paper holder 10.

The holder 10 is composed of a common disposable material such that it may be disposed of after the first use. The disposable material may be any one of a variety of disposable materials approved by the United States Food and Drug Administration (FDA) to be used inside a patient's mouth. One example of the disposable material is ABS plastic which is a special plastic material approved by FDA. Such a material is relatively economical and readily moldable. Also, the design of holder 10 is such that it can be produced by a single mold and in a one-step operation.

The dimensions are selected so as to provide an adequate size for the dentist to manipulate while anchoring the necessary amount of material. With the structure 10, the length "$l_1$" of holding arm 16 is approximately 2.25 inches, the length "$l_2$" of holding arm 16 is approximately 2.1875 inches, the width "$w_1$" of the arms 14 and 16 is approximately 0.1875 inches, the outer width "$w_2$" of the handle 12 is approximately 0.05 inches and the thickness "d" of the handle 12 and arms 14 and 16 are approximately 0.125 inches, though the arms 14 and 16 are slightly tapered towards their terminal ends.

FIG. 5 shows a top view of an alternative embodiment of a paper holder according to the present invention and referred to by the general reference character 30. A handle 32 and a holding arm 34 are similar disposed as the arm 12 and arm 14 of FIGS. 1–4, with a locking arm 36 loosely coupled and attached to the holding arm longitudinally along a hinge 37. A plurality of dents 38 and a coinciding plurality buttons 42 are also used as the locking means to firmly hold the articulating paper in place. The longitudinal coupled and attached locking arm 36 shortens the necessary distance of moving the locking arm 36 toward the holding arm 34 when locking articulating paper in place. The structure 30 may be comprised of the same material and dimensions as those of the holder 10. Also, the hinge 37 may be of the same material but of less thickness such that the holder 30 may be made in a single mold in a one-step process.

FIG. 6 shows a top view of an another alternative embodiment of a holder according to the present invention and referred to by the general reference character 50 wherein a handle 52, and a holding arm 54 are similar to the handle 12 and arm 14 of FIGS. 1–4 of the paper holder 10. However, a locking arm 56 is detached from the handle 52 and the holding arm 54 prior to assembly. Thus, the locking arm 56 may be independently and separately disposed. Holding arm 54 and locking arm 56 also have a coinciding sets of dents 58 and buttons 62 as that of paper holder 10 to lock and firmly hold the articulating paper. The holder 50 may have the advantage that by producing the handle 52 and the holding arm 54 as one integral piece and the locking arm 56 as an independent and separate piece, the manufacturing process may be further simplified thereby having a lower production cost.

FIGS. 7A and 7B show a further alternative embodiment of a holder according to the present invention and referred to by the general reference character 70 wherein a handle 72, a holding arm 74, and a locking arm 76 are similar disposed as that shown in FIGS. 1 to 4 of the paper holder 10 (FIG. 7A) except that both the holding arm 74 and the locking arm 76 are foldable along a fold line 77 so that for disposal both arms can be folded into the interior space of the handle 72. The holding arm 74 and the locking arm 76 can each be positioned to extend forward from the handle 72 when in use. Holding arm 74 and locking arm 76, have dents 78 and buttons 82, respectively to lock and firmly hold the articulating paper. The paper holder 70 may have the advantage that it may be shipped and stored in a more compact and space-saving way.

There can be a wide variety of the designs for the handle, the holding arm, the locking arm and the locking means. For example, to further reduce the risk of repeated use of a holder, the locking means may be designed so that once the locking arm is locked to the holding arm it becomes very difficult to unlock or even if unlocked, it cannot be reused. Alternatively, the attachment of the locking arm to either the handle or the holding arm can be designed such that the attachment is severed once a locking is performed such that a clear indication is provided showing that a holder was previously used. For a foldable and extendable paper holder, the extending fixture which is used to maintain the holding arm in an extended position may be designed such that once a holding arm is unfolded it is prevented from being folded again.

Although the present invention has been described in terms of the presently preferred embodiment, it is to be understood that such disclosure is not to be interpreted as limiting. Various alternations and modifications will no doubt become apparent to those skilled in the art after reading the above disclosure. Accordingly, it is intended that the appended claims be interpreted as covering all alternations and modifications as fall within the true spirit and scope of the invention.

I claim:

1. An articulating paper holder comprising:
   an elongated handle;
   an elongated holding arm securely attached to and extending from the handle;
   a holding means for securely holding to the holding arm a piece of articulating paper for imprinting occlusal contact patterns, the elongated holding arm and the holding means being foldable onto and extendable from the elongated handle whereby the holding arm can be folded and protected by the handle when the holding arm is not in use.

2. The articulating paper holder of claim 1 wherein:
   the elongated handle and the elongated holding arm are composed of a disposable plastic material whereby the articulating paper holder may be mass produced and disposable.

3. The articulating paper holder of claim 2 wherein:
   said disposable material comprises United States Food and Drug Administration (FDA) approved ABS plastic.

4. The articulating paper holder of claim 2 wherein:
   the holding means includes an elongated locking arm having a locking means for securely locking to the holding arm and to articulating paper whereby said articulating paper may be firmly held in position by the holding arm and said locking arm.

5. The articulating paper holder of claim 4 wherein:
   said locking means may be unlocked after locking for separating said locking arm from the holding arm whereby said articulating paper may be readjusted relative to said locking arm and the holding arm.

6. The articulating paper holder of claim 5 wherein:
   said locking arm is aligned with the holding arm and pivotable about one end of the holding arm such that it may be folded over the holding arm.

7. The articulating paper holder of claim 6 wherein:
   said locking arm is of substantially equal length with the holding arm and of less length than the handle.

8. The articulating paper holder of claim 7 wherein:
   the holding arm has a first facial surface and said locking arm has a second facial surface opposite said first facial surface;
   said locking means including a plurality of dents disposed on said first facial surface and a plurality of corresponding buttons disposed on said second facial surface wherein said corresponding buttons may be pressed into said dents for securely locking said locking arm to the holding arm.

9. The articulating paper holder of claim 7 wherein:
   said locking arm is severed from the holding arm once said locking arm is locked to the holding arm whereby a clear showing of a prior locking is provided.

10. The articulating paper holder of claim 6 wherein:
    the holding arm has a first facial surface and said locking arm has a second facial surface opposite said first facial surface;
    said locking means includes a plurality of dents disposed on said first facial surface and a plurality of corresponding buttons disposed on said second facial surface wherein said corresponding buttons may be pressed to insert in said dents for securely locking said locking arm to the holding arm.

11. The articulating paper holder of claim 10 wherein:
    said locking arm is severed from the holding arm once said locking arm is locked to the holding arm whereby a clear showing of a prior locking is provided.

12. An articulating paper holder comprising:
    an elongated handle, an elongated holding arm, and a locking arm, all composed of disposable material;
    the elongated holding arm being securely attached to and extending from one end of the handle having a first facial surface with a plurality of dents disposed thereon;
    the locking arm being of substantially equal length with and foldably attached to the holding arm and pivotable about said end, including a second facial surface with a plurality of corresponding buttons corresponding to said dents and disposed to align with said corresponding dents as the locking arm is pushed with said first and second facial surfaces interfacing for securely locking the locking arm to the holding arm and securely holding a piece of articulating paper for imprinting occlusal contact patterns; and
    the locking arm being severed from the holding arm about said end once said locking arm locks to the holding arm whereby a clear showing of a prior locking is provided.

13. An articulating paper holder comprising:
    an elongated handle;
    an elongated holding arm securely attached to and extending from the handle for a piece of articulating paper for imprinting occlusal contact patterns;
    an elongated locking arm for engaging said piece of articulating paper, the elongated locking arm being engaged about one end of the handle and pivotable about said end and foldable onto the holding arm and extending from the handle; and
    locking means integral with the holding arm and the locking arm for securely locking said articulating paper in place between the locking arm and holding arm.

14. The articulating paper holder of claim 13 wherein,
    said locking means includes at least one dent and at least one button, with said button interlocking with said dent when the locking arm is folded onto the holding arm.

15. The articulating paper holder of claim 14 wherein,
    said locking means includes a plurality of dents and a plurality of buttons with each button interlocking with one of said dents when the locking arm is folded onto the holding arm.

* * * * *